US007041255B2

(12) United States Patent
Wang

(10) Patent No.: US 7,041,255 B2
(45) Date of Patent: May 9, 2006

(54) DETECTION OF DENGUE VIRUS

(75) Inventor: Wei-Kung Wang, Taipei (TW)

(73) Assignee: National Health Research Institute, Taipei (TW)

( * ) Notice: Subject to any disclaimer, the term of this patent is extended or adjusted under 35 U.S.C. 154(b) by 432 days.

(21) Appl. No.: 10/085,944

(22) Filed: Feb. 28, 2002

(65) Prior Publication Data

US 2002/0155435 A1 Oct. 24, 2002

Related U.S. Application Data

(60) Provisional application No. 60/272,535, filed on Mar. 1, 2001.

(51) Int. Cl.
*B01L 3/00* (2006.01)
(52) U.S. Cl. .................. 422/61; 536/24.33; 424/218.1
(58) Field of Classification Search ................. 422/61; 536/24.33; 424/218.1
See application file for complete search history.

(56) References Cited

U.S. PATENT DOCUMENTS 5,939,254 A 8/1999 Ennis et al. ................... 435/5

FOREIGN PATENT DOCUMENTS

WO WO-96/40933 A1 * 12/1996

OTHER PUBLICATIONS

Kawano, H., et al., 1993, "Genetic determinants of dengue type 4 virus neurovirulence for mice", J. Virol. 67(11):6567-6575.*

Mellors, et al. *Prognosis in HIV-I Infection Predicted by the Quantity of Virus in Plasma.* Science, vol. 272, May 24, 1996, pp. 1167-1170.

Seah, et al. *Rapid, single-step RT-PCR typing of dengue viruses using five NS3 gene primers.* Journal of Virological Methods, vol. 51, 1995, pp. 193-200.

Pierre, et al. *Identification of mosquito-borne favivirus sequences using universal primers and reverse transcription/polymerase chain reaction.* Res. Virol. vol. 145, 1994, pp. 93-104.

Chang, et al. *An Integrated Target Sequence and Signal Amplification Assay, Reverse Transcriptase-PCR-Enzyme-Linked Immunosorbent Assay, To Detect and Characterize Flaviviruses.* Journal of Clinical Microbiology, vol. 32, No. 2, Feb. 1994, pp. 477-483.

Morita, et al. *Rapid Identification of Dengue Virus Serotypes by Using Polymerase Chain Reaction.* Journal of Clinical Microbiology, vol. 29, No. 10, Oct. 1991, pp. 2107-2110.

Morita, et al. *Rapid Detection of Virus Genome from Imported Dengue Fever and Dengue Hemorrhagic Fever Patients by Direct Polymerase Chain Reaction.* Journal of Medical Virology, vol. 44, 1994, pp. 54-58.

Lanciotti, et al. *Rapid Detection and Typing of Dengue Viruses from Clinical Samples by Using Reverse Transcriptase-Polymerase Chain Reaction.* Journal of Clinical Microbiology, vol. 30, No. 3, Mar. 1992, pp. 545-551.

Henchal, et al. *Sensitivity and Specificity of a Universal Primer Set for the Rapid Diagnosis of Dengue Virus Infections by Polymerase Chain Reaction and Nucleic Acid Hybridization.* Am. J. Trop. Med. Hyg. 45(4), 1991, pp. 418-428.

Deubel, et al. *Identification of dengue sequences by genomic amplification: rapid diagnosis of dengue virus serotypes in peripheral blood.* Journal of Virological Methods, 30 (1990), pp. 41-54.

Chungue, et al. *Ultra-Rapid, Simple, Sensitive, and Economical Silica Method for Extraction of Dengue Viral RNA From Clinical Specimens and Mosquitoes by Reverse Transcriptase-Polymerase Chain Reaction.* Journal of Medical Virology, vol. 40, 1993, pp. 142-145.

Chan, et al. *The influence of antibody levels in dengue diagnosis by polymerase chain reaction.* Journal of Virological Methods, vol. 49, 1994, pp. 315-322.

Wang, et al. *Quantitative Competitive Reverse Transcription-PCR for Quantification of Dengue Virus RNA.* Journal of Clinical Microbiology, vol. 38, 2000, pp. 3306-3310.

* cited by examiner

*Primary Examiner*—Jeffrey S. Parkin
(74) *Attorney, Agent, or Firm*—Fish & Richardson P.C.

(57) ABSTRACT

The present invention relates to a pair of dengue virus-specific primers for use in a reverse transcriptase-polymerase chain reaction to detect dengue virus.

18 Claims, No Drawings

SEQUENCE LISTING

```
<160> NUMBER OF SEQ ID NOS: 2

<210> SEQ ID NO 1
<211> LENGTH: 28
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: 9, 13, 14
```

-continued

```
<223> OTHER INFORMATION: n = inosine

<400> SEQUENCE: 1
cccatctcnt cannatccct gctgttgg                                              28

<210> SEQ ID NO 2
<211> LENGTH: 28
<212> TYPE: DNA
<213> ORGANISM: Artificial Sequence
<220> FEATURE:
<223> OTHER INFORMATION: Primer

<400> SEQUENCE: 2
aatatgctga aacgcgagag aaaccgcg                                              28
```

DETECTION OF DENGUE VIRUS

RELATED APPLICATIONS

This application claims priority to U.S. provisional application No. 60/272,535 filed on Mar. 1, 2001, the contents of which are incorporated herein by reference.

FIELD OF THE INVENTION

This invention relates to methods and reagents for detecting dengue viruses.

BACKGROUND OF THE INVENTION

Dengue virus, a member of flaviviruses, contains an 11 kb single-stranded RNA genome. Four different dengue virus subtypes have been identified, i.e., DEN-1, DEN-2, DEN-3, and DEN-4. The four subtypes are distributed among geographically distinct tropical and subtropical regions. All may cause diseases ranging from mild self-limited dengue fever (DF) to severe and potentially life-threatening dengue hemorrhagic fever/ dengue shock syndrome (DHF/DSS). Gubler, D. J. (1998) *Clin. Microbiol. Rev.* 11: 480–496. Detection of dengue virus is crucial for rapid diagnosis, as well as for understanding of dengue virus pathogenesis. Innis, B. L. (1995) In J. S. Porterfield (Ed.), *Exotic viral infections*—1995. Chapman & Hall, London, pp103–146.

SUMMARY OF THE INVENTION

The present invention is based on the development of a pair of dengue virus-specific primers for use in a reverse transcriptase-polymerase chain reaction (RT-PCR) to detect dengue virus. The term "detect" as used herein refers to either qualitative or quantitative identification of dengue virus.

One aspect of this invention relates to either of the two primers in such a pair of dengue virus-specific primers: e.g., a 28-mer 5'-CCCATCTCITCAIIATCCCTGCTGTTGG-3 ' (SEQ ID NO:1) or a fragment thereof containing at least 18 nucleotides, and another 28-mer 5'-AATATGCT-GAAACGCGAGAGAAACCGCG-3'(SEQ ID NO:2) or a fragment thereof containing at least 18 nucleotides.

In another aspect, this invention relates to a method of qualitatively identifying dengue virus in a sample. The method includes obtaining a sample that is suspected of containing dengue viral RNA, performing a RT-PCR on the sample with a reverse transcriptase, a polymerase, and a pair of dengue virus-specific primers as described above, to amplify the dengue viral RNA, if present, and detecting the amplification product as an indication of presence of dengue virus in the sample.

In a further aspect, this invention relates to a method of quantitating dengue virus in a sample. The method includes obtaining a sample that is suspected of containing dengue viral RNA, mixing the sample with a known amount of a competitor nucleic acid, and performing a RT-PCR on both the sample and the competitor nucleic acid with a reverse transcriptase, a polymerase, and a pair of dengue virus-specific primers as described above, to amplify the dengue virus RNA, if present, and the competitor nucleic acid. The competitor nucleic acid, either a DNA or a RNA, can be amplified by using a pair of dengue virus-specific primers of this invention, and its amplification product is detectably different from that of dengue viral RNA (e.g., due to a shorter or a longer length). Preferably, the competitor nucleic acid is identical to dengue viral RNA, except having an insertion into or a deletion from dengue viral RNA. When a RT-PCR is performed, both dengue viral RNA in a sample and a competitor nucleic acid at a known concentration are amplified, and quantitation of the dengue virus is achieved by comparing the amount of the amplification product of the dengue viral RNA, if present, to that of the amplification product of the competitor nucleic acid.

This invention also features a kit for detecting dengue virus. The kit includes a pair of dengue virus-specific primers as described before. It may also include one or more other reagents such as a competitor nucleic acid, a reverse transcriptase, a polymerase, nucleosides, or a reaction buffer.

Also within the scope of this invention is an isolated nucleic acid containing a fragment of a dengue viral RNA genome or a DNA copy thereof, wherein the fragment includes a first sequence that is complementary or identical to at least 18 nucleotides of SEQ ID NO:1, a second sequence that is complementary or identical to at least 18 nucleotides of SEQ ID NO:2, and a non-naturally occurring deletion or insertion, the deletion or insertion occurring in a region of the fragment flanked by the first and the second sequence. Preferably, the non-naturally occurring deletion or insertion is 30 to 50 nucleotides. Such a nucleic acid can be a competitor RNA used in the above-described method for quantitating dengue virus. It can also be a plasmid, from which the competitor RNA can be generated by in vitro transcription. One example of the plasmid is Cd40PrM/pCR3.1 as described in the actual examples provided below.

Other features and advantages of the invention will be apparent from the detailed description and the claims.

DETAILED DESCRIPTION OF THE INVENTION

The present invention relates to the use of a pair of novel dengue virus-specific primers, SEQ ID NOs:1 and 2, in a RT-PCR method for detecting dengue virus.

The term "primer" as used herein refers to an oligonucleotide capable of acting as a point of initiation of synthesis of a primer extension product that is complementary to a nucleic acid strand (template or target sequence), when placed under suitable conditions (e.g., salt concentration, temperature, and pH) in the presence of nucleotides and other reagents for nucleic acid polymerization (e.g., a DNA dependent or RNA dependent polymerase). SEQ ID NO:1 corresponds to genome positions 278 to 305 of DEN-2 Jamaica strain, including deoxyinosine residues located at nucleotide 9, 13, and 14 of SEQ ID NO:1. SEQ ID NO:2, on the other hand, corresponds to genome positions 136 to 163 of the same strain. This primer pair, SEQ ID NOs:1 and 2, targets a region in the capsid of all four subtypes of dengue virus, e.g., Hawaii strain (DEN-1), New Guinea strain (DEN-2), H-87 strain (DEN-3), and H-241 strain (DEN-4), but not that of other flaviviruses, e.g., the Japanese encephalitis virus (JEV).

As known in the art, a primer must be of a sufficient length to prime the synthesis of extension products. A typical primer contains at least 10 nucleotides, and is substantially complementary or homologous to the target sequence. The dengue virus-specific primers of the present invention can be a nucleic acid of 18 to 28 nucleotides in length and including 28 nucleotides of SEQ ID NO:1 or 2, or a fragment thereof which contains at least 18 consecutive nucleotides of SEQ ID NO:1 or 2. For example, one primer of this invention can be a 18-mer or 23-mer, and includes at least 18 or 23 consecutive nucleotides of SEQ ID NO:1 or SEQ ID NO:2.

As another example, it can be a 28-mer in which only 18 or 23 nucleotides constitute a sequence identical to a segment of SEQ ID NO:1 or 2. The lengths of the two primers in a pair may not be the same.

The just-described primers can be prepared by synthetic or recombinant method. A RT-PCR assay is employed to determine whether any of them can be used to practice the method of detecting or quantitating dengue virus. More specifically, a pair of primers is used in a RT-PCR to determine their ability to amplify all four subtypes of dengue viral RNA, as well as their inability to amplify a representative number of other flaviviruses. A pair of primers to be used to practice this invention can be designed based on analysis of all available sequences of dengue viruses and other flaviviruses in the GenBank. A pair of primers thus designed can be further analyzed by any related software program of their properties, e.g., annealing temperature, or internal pairing. To test their ability to detect all four dengue viruses, a RT-PCR, containing the primer pair, a RNA template derived from one of the four types of dengue viruses and at least one of other flaviviruses such as JEV, can be performed under the conditions described in the actual examples presented below. An annealing temperature in the RT-PCR (e.g., 65° C. ) can be modified according to the annealing temperature of the designed primer pair. In a designed primer that covers nucleotides located at 9, 13 and 14 of SEQ ID NO:1, deoxy-inosine residues may be used at these positions in order to efficiently detect all four dengue viruses.

To practice the method of this invention for detecting dengue virus, a RT-PCR is performed using a reverse transcriptase, a polymerase, and a pair of dengue virus-specific primers of this invention to amply dengue viral RNA in a sample. The sample can be a culture supernatant or a plasma specimen prepared from a dengue virus infected individual. The pair of dengue virus-specific primers of this invention is capable of amplifying dengue viral RNA from all four different dengue virus subtypes. Despite the variation of dengue virus subtypes, the products amplified by the dengue virus-specific primers, unexpectedly, have the same or similar lengths of about 170-bp. Generating amplified products of the same or similar sizes for all four subtypes increases the sensitivity of detecting dengue virus in a sample from an individual infected by multiple dengue virus subtypes. Lorono-Pino, et al. (1999) *Am J Trop Med Hyg* 61:725–730. It should be noted that using a previously published RT-PCR method for detecting dengue virus (Lanciotti, et al. (1992) *J Clin Microbiol* 30: 545–551, and Harris, et al. (1998) *J Clin Microbiol* 36: 2634–2639) can produce a RT-PCR product of 511-bp in a first round PCR, and products of 482-bp, 119-bp, 290-bp, and 392-bp in a second round PCR for DEN-1, DEN-2, DEN-3, and DEN-4, respectively.

A method of quantitating dengue virus is also within the scope of this invention. More specifically, a RT-PCR is performed on a sample (more precisely, the dengue viral RNA is in it, if any) and a competitor nucleic acid at a known concentration by using a pair of primers described above. Quantitation of any dengue virus in the sample can be achieved by separating the amplification products of the dengue viral RNA and the competitor nucleic acid, and then determining their relative amounts. For example, by using SEQ ID NOs:1 and 2 and a competitor nucleic acid which, when amplified, provides a 130-bp product, a 170-bp amplification product of the dengue virus, if any, and a 130-bp amplification product of the competitor nucleic acid are obtained. The two products can be separated by gel electrophoresis or other size-discriminating chromatography. Each amplification product can be visualized and quantitated by ethidium bromide staining, autoradiography, radiographic counting, densitometry, or any other suitable techniques. The copy number of dengue virus RNA in the sample can be calculated based on the initial copy number of the competitor nucleic acid and the ratio of the amount of the amplification product of the dengue virus RNA to that of the competitor nucleic acid. Unexpectedly, this method can detect as few as 10 to 50 copies of dengue viral RNA. In such a sensitive assay, using the competitor nucleic acid as an internal control is particularly critical for a clinical sample, in which the presence of an inhibitor or other variables might affect the kinetics and efficiency of the RT-PCR.

This invention further features an isolated nucleic acid containing a segment of a dengue viral RNA genome, wherein the nucleic acid includes a non-naturally occurring deletion or insertion. Such a nucleic acid is used as a competitor RNA in the above-described method for quantitating dengue virus, and can be prepared by in vitro transcription.

The specific examples below are to be construed as merely illustrative, and not limitative of the remainder of the disclosure in any way whatever. Without further elaboration, they are believed that one skilled in the art can, based on the description herein, utilize the present invention to its fullest extent. All publications recited herein are hereby incorporated by reference in their entirety.

EXAMPLE 1

Detection of RT-PCR Using Dengue Virus-Specific Primers

Dengue viral RNA was isolated from aliquots of plasma samples and culture supernatants, using the QIAamp viral RNA mini kit (Qiagen, Germany). Two plasma samples were obtained within 24 hours of the onset of fever of two confirmed DF patients during a DEN-3 outbreak in southern Taiwan in 1998. Four plasma samples were obtained from two hepatitis C virus (HCV) carriers and two healthy individuals. Stock virus samples of the four dengue serotypes, Hawaii (DEN-1), New Guinea (DEN-2), H-87 (DEN-3), and H-241 (DEN-4) strains, had titers of $2.1 \times 10^6$ pfu/ml, $1.3 \times 10^6$ pfu/ml, $2 \times 10^6$ pfu/ml and $1 \times 10^6$ pfu/ml, respectively. The four stock virus samples were obtained from culture supernatants of infecting mosquito C6/36 cells and then titrated on BHK-21 cells by a standard plaque-forming assay. Other samples, i.e., three Japanese encephalitis virus (JEV) strains (Nakayama vaccine strain, Beijing vaccine strain, and CH1949 Taiwan local strain isolated from Changhwa County) with titers ranged from $10^5$ to $10^6$ pfu/ml, were also used for comparison. JEV, a flavivirus, is not a dengue virus. For a RT-PCR, one to one hundred-fold dilutions of stock virus samples were used. For a quantitative competitive RT-PCR (QC-RT-PCR), one to ten thousand-fold dilutions of the Hawaii virus sample and serial two-fold dilutions thereafter, were used. Briefly, 140 µl of plasma samples or diluted stock virus samples were mixed with a buffer AVL/a carrier RNA, and loaded onto spin columns, followed by washing with buffer AW and eluting with a buffer AVE to a final volume of 50 µl, as recommended by the manufacturer (Qiagen, Germany).

Two dengue virus-specific primers, SEQ ID NO:1 and SEQ ID NO:2 were used to detect dengue viral RNA. RNA templates derived from culture supernatants of virus samples representing all four dengue serotypes: Hawaii (DEN-1), New Guinea (DEN-2), H-87 (DEN-3), and H-241 (DEN-4), were amplified by RT-PCR reactions. After amplification, products were electrophoresed through 2% agarose gel and stained with ethidium bromide. Amplification products of the expected size of 170-bp were observed in the reactions using the RNA templates derived from all four dengue viruses. As a control, there was no product observed in the reactions containing no RNA or when only PCR (no RT) was performed. RNA templates derived from other flavivirus samples, three JEV and two HCV, as well as from plasma samples of two healthy individuals, were also amplified by RT-PCR reactions. None of RNA templates had been amplified to generate products of the expected size. These results show that the dengue virus-specific primers were able to detect all four dengue virus subtypes but not other flaviviruses tested.

EXAMPLE 2

Quantitation of Recombinantly Prepared Dengue Viral RNA

CPrM/pCR3.1 is a plasmid containing the entire capsid region and the N-terminal 54 amino acids of the precursor membrane (PrM) region of DEN-2 strain PL046 in the vector pCR3.1 (Invitrogen, San Diego). See Lin, et al. (1998) *J Virol.* 72: 9729–9737, and U.S. Pat. Nos. 5,487,993 and 5,827,657. A competitor construct, Cd40PrM/pCR3.1, was modified from CPrM/pCR3.1 by digestion with two restriction enzymes, SalI and BsmI, in the capsid region, followed by filling the 3' recessed end (from SalI cut) and removing the 5' protruding end (from BsmI cut) with T4 DNA polymerase. Compared to CPrM/pCR3.1, Cd40PrM/pCR3.1 had a 40-bp internal deletion in the capsid region, as verified by DNA sequencing. A competitor RNA, which was generated from in vitro transcription (Promega, Madison) of the linearized Cd40PrM/pCR3.1, was purified by phenol/chloroform extraction and quantitated by spectrophotometer. See Melton, et al. (1984) *Nucl. Acids Res.* 12: 7035. The copy number of the competitor RNA was calculated based on the concentration measured and its molecular weight. Wild-type dengue viral RNA was generated from the linealized CPrM/pCR3.1 and quantitated by spectrophotometer as well. The copy number of the dengue viral RNA was also calculated from the concentration measured and its molecular weight, and known amounts of the dengue viral RNA were used as a target RNA in a QC-RT-PCR assay.

As described previously, a dengue viral RNA template was obtained from a plasma sample, and was further diluted ten-fold. Equal amounts (2 µl) of the RNA template or its diltute were mixed with increasing copy numbers of the competitor RNA obtained from the above experiment (0, 10, 50, 100, 500, 1000, 5000, 10000 copies), and were amplified by RT-PCR reactions using the Superscript one-step RT-PCR system (Giboco/BRL, Life technologies). The RT-PCR reaction conditions were 55° C. for 40 min, and 94° C. for 2 min, followed by 40 cycles of 94° C. for 45 sec, 65° C. for 45 sec, and 68° C. for 45 sec. For a control, a RNA template (2 µl) was amplified by PCR using super Taq DNA polymerase (HT Biotechnology, Cambridge, England) under the same PCR conditions as those in the RT-PCR, except that the step of using 55° C. for 40 min was omitted.

The QC-RT-PCR products were electrophoresed through 2% agarose gel and stained with ethidium bromide. The amplification product of dengue viral RNA was 170-bp, and the amplification product of the competitor RNA was 130-bp. The amounts of the 170-bp and 130-bp products were measured under UV light using a digital gel documentation analysis system consisting of a UV-transilluminator light box, a darkroom cabinet, and a digital camera, DigiPix™ (Ultralum, Paramount, Calif.). The image acquired with the digital camera was sent to the computer directly and was analyzed by the software 1D scan (Scanalytics, Fairfax, Va.). The intensity of the ethidium fluorescence associated with the DNA band was proportional to the amount of DNA. Since the comparisons in the QC-RT-PCR were based on the molar amounts, the fluorescence intensity of the 130-bp product was corrected by a factor of 170/130 to enable direct comparison of the corrected 130-bp intensity (Cor. Int.) with the fluorescence intensity of the 170-bp. The ratios of the corrected intensity of 130-bp to the intensity of- 170 bp (Cor. Int. 130/int. 170) (in log scale) were plotted against the copy number of the competitor RNA (in log scale). A regression line with the coefficient of determination was generated. The copy numbers of dengue viral RNA per reaction were determined by interpolated assessment of the equivalence point of the above curve. The 95% confidence intervals (CI) of the copy numbers were calculated using the software SPSS base 8.0 (SPSS Inc., Chicago, Ill.). Since 2 µl out of 50 µl RNA templates, which were derived from 140 µl culture supernatants or plasma samples, were used in each reaction, the number of dengue RNA copies per reaction was divided by 5.6 µl (140 µl×2 µl /50 µl) and multiplied by 1000 to obtain the number of dengue viral RNA copies per ml of culture supernatants or plasma samples.

To assess the feasibility of the QC-RT-PCR assay in quantitation, a known amount of in vitro transcribed target and a competitor RNA (both obtained from Example 2) were used in a QC-RT-PCR amplification. As described in Example 2, in this amplification reaction increasing amounts of the competitor RNA (0, 10, 50, 100, 500, 1000, 5000, and 10000 copies) and identical amounts of the target RNA (300 copies) were used, and resulting in a gradual increase of the 130-bp product of the competitor RNA and a gradual decrease of the 170-bp product of the target. The point where the band intensity of the 130-bp product derived from a known amount of the competitor RNA corresponded to the intensity of the 170-bp product in molar equivalence indicated the amount of the target RNA present in the sample. After correction of the intensity of the 130-bp product by a factor of 170/130, the ratios of the corrected intensity (Cor. Int.) of the 130-bp band to the intensity of the 170-bp band in log scale [log (Cor. Int. 130/Int. 170)] were plotted against the copy number of the competitor RNA in log scale. A regression line was obtained. The point at which the ratio of Cor. Int. 130 to Int. 170 equals 1 represents the amount of the target RNA present in the sample. The amount of the target RNA was thus determined to be 302 copies (95% CI: 224 to 388 copies), which was unexpectedly close to the actual amounts of 300 copies added in each reaction.

To demonstrate the accuracy of quantitation of the QC-RT-PCR assay, different amounts of the target RNA, ranging from 10 copies to 2000 copies, were tested, and the numbers of copies determined were very close to the actual copies added to respective reactions. From continuing optimization of the assay, the sensitivity of the assay was estimated to be between 10 to 50 copies of RNA per reaction.

EXAMPLE 3

Quantitation of Dengue Viral RNA in Culture Supernatants

To evaluate the QC-RT-PCR assay on samples other than the target RNA obtained from Example 2, dengue viral RNA isolated from DEN-1 virus sample (prepared by the method described in Example 1, a Hawaii strain) was amplified by a QC-RT-PCR amplification. As described in Example 2, in this amplification reaction increasing amounts of the competitor RNA (0, 10, 50, 100, 500, 1000, and 5000 copies) and identical amounts of dengue viral RNA were used, and resulting in a gradual increase of the 130-bp product of the competitor RNA and a gradual decrease of the 170-bp product of the target. The ratios of the corrected intensity of the 130-bp product to the intensity of the 170-bp product in log scale [log (Cor. Int. 130/Int. 170)] were plotted against the copy number of the competitor RNA in log scale. Based on the regression line obtained, the amount of dengue viral RNA was determined to be 205 copies (95% CI: 109 to 388 copies) per reaction, which corresponded to 36,607 copies RNA per ml of supernatant.

To further evaluate this QC-RT-PCR assay, serial two-fold dilutions of the DEN-1 Hawaii strain were used in QC-RT-PCR reactions. The dengue viral RNA copy numbers were determined for each dilution and plotted against the virus titer of each dilution. A linear relationship was observed between the determined dengue viral RNA copy numbers per ml of supernatant and the virus titer represented as plaque forming units (pfu) per ml, and two-fold difference in virus titer would be differentiated by this QC-RT-PCR assay.

EXAMPLE 4

Quantitation of Dengue Viral RNA in Plasma Samples

QC-RT-PCR amplifications were performed on samples prepared from two DEN-3 infected individuals in a manner as described in Example 1. As described in Example 2, in amplification reactions increasing amounts of the competitor RNA (0, 10, 50, 100, 500, 1000, 5000, and 10000 copies) and identical amounts of dengue viral RNA in the samples were used. The same results were obtained from the two samples. A gradual decrease in the intensity of the 170-bp product of dengue viral RNA and a gradual increase in the intensity of the 130-bp products of competitor RNA were observed as the amounts of the competitor increased from 0 to 10000 copies. The ratios of the corrected intensity of the 130-bp band to the intensity of 170-bp band in log scale [log (Cor. Int. 130/Int. 170)] were plotted against the copy number of the competitor RNA in log scale. The amount of dengue viral RNA was determined to be 170 copies (95% CI: 89 to 359 copies) per reaction, which corresponded to 303,570 copies of RNA per ml of plasma for one sample. The amount of RNA was determined to be 39 copies (95% CI: 18 to 115 copies) per reaction, corresponding to 69,640 copies of RNA per ml of plasma for the other sample. The identity of the 170-bp RT-PCR products was confirmed to be dengue viral capsid after cloning and sequencing of the 170-bp bands for the two samples.

OTHER EMBODIMENTS

A number of embodiments of the invention have been described. Nevertheless, it will be understood that various modifications may be made without departing from the spirit and scope of the invention. For example, a nucleic acid having one- or two-base variations in the sequence of any of the above-described primers can also be tested and used to practice the present invention. In another example, also within this invention is a nucleic acid of 10 to 50 nucleotides in length and containing at lease 10 consecutive nucleotides of SEQ ID NO:1 or 2. Accordingly, other embodiments are within the scope of the following claims.

What is claimed is:

1. A kit for detecting dengue virus comprising:
   A first dengue virus-specific primer, which is 18 to 28 nucleotides in length and includes at least 18 nucleotides of SEQ ID NO:1; and
   A second dengue virus-specific primer, which is 18 to 28 nucleotides in length and includes at least 18 nucleotides of SEQ ID NO:2.

2. The kit of claim 1, further comprising a known amount of a competitor nucleic acid with length detectably different from the dengue virus RNA.

3. The kit of claim 1, wherein the first dengue virus-specific primer is 18 to 23 nucleotides in length.

4. The kit of claim 1, wherein the first dengue virus-specific primer is the nucleotide sequence of SEQ ID) NO:1.

5. The kit of claim 1, wherein the second dengue virus-specific primer is 18 to 23 nucleotides in length.

6. The kit of claim 1, wherein the second dengue virus-specific primer is the nucleotide sequence of SEQ ID NO:2.

7. The kit of claim 3, wherein the second dengue virus-specific primer is 18 to 23 nucleotides in length.

8. The kit of claim 4, wherein the second dengue virus-specific primer is the nucleotide sequence of SEQ ID NO:2.

9. A nucleic acid, which is 18 to 28 nucleotides in length and includes at least 18 consecutive nucleotides of SEQ ID NO:1.

10. The nucleic acid of claim 10, wherein the nucleic acid is 18 to 23 nucleotides in length and includes at least 18 consecutive nucleotides of SEQ ID NO:1.

11. The nucleic acid of claim 9, wherein the nucleic acid is the nucleotide sequence of SEQ ID NO:1.

12. A nucleic acid, which is 18 to 25 nucleotides in length and includes at least 18 consecutive nucleotides of SEQ ID NO:2.

13. The nucleic acid of claim 12, wherein the nucleic acid is 18 to 23 nucleotides in length and includes at least 18 consecutive nucleotides of SEQ ID NO:2.

14. A nucleic acid, wherein the nucleic acid is the nucleotide sequence of SEQ ID NO:2.

15. An isolated nucleic acid comprising a fragment of a dengue viral genome or a DNA copy thereof, wherein the fragment includes:
   a first sequence that is complementary or identical to at least 18 consecutive nucleotides of SEQ ID NO:1;
   a second sequence that is complementary or identical to at least 18 consecutive nucleotides of SEQ ID NO:2; and
   a non-naturally occurring deletion or insertion, the deletion or insertion occurring in a region of the fragment flanked by the first and the second sequence.

16. The nucleic acid of claim 15, wherein the first sequence is complementary or identical to SEQ ID NO:1 and the second sequence that is complementary or identical to SEQ ID NO:2.

17. The nucleic acid of claim 15, wherein the nucleic acid is consists of:
   a first sequence that is complementary or identical to at least 18 consecutive nucleotides of SEQ ID NO:1;
   a second sequence that is complementary or identical to at least 18 consecutive nucleotides of SEQ ID NO:2; and
   a third sequence that is flanked by the first and second sequence, wherein the third sequence is complementary or identical to a genomic Dengue virus region that is (a) naturally flanked by the first and the second sequence and (b) includes a non-naturally occurring deletion or insertion.

18. The nucleic acid of claim 17, wherein the first sequence is complementary or identical to SEQ ID NO:1 and the second sequence is complementary or identical to SEQ ID NO:2.

* * * * *